United States Patent
Marrow et al.

(10) Patent No.: US 7,483,129 B2
(45) Date of Patent: Jan. 27, 2009

(54) ON-LINE PROPERTIES ANALYSIS OF A MOLTEN POLYMER BY RAMAN SPECTROSCOPY FOR CONTROL OF A MIXING DEVICE

(75) Inventors: David Geoffrey Marrow, Taylor Lake Village, TX (US); David A. Yahn, Humble, TX (US); Thomas R. Veariel, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 356 days.

(21) Appl. No.: 11/188,277

(22) Filed: Jul. 22, 2005

(65) Prior Publication Data
US 2007/0019190 A1    Jan. 25, 2007

(51) Int. Cl.
*G01J 3/44* (2006.01)
(52) U.S. Cl. .................................................. 356/301
(58) Field of Classification Search ................. 356/301; 526/72, 64, 68, 901, 905, 348.3, 348.4, 348.6, 526/348.5
See application file for complete search history.

(56) References Cited

U.S. PATENT DOCUMENTS

| | | |
|---|---|---|
| 3,725,378 A | 4/1973 | Chamberlin |
| 3,779,712 A | 12/1973 | Calvert et al. |
| 4,175,169 A | 11/1979 | Beals et al. |
| 4,182,810 A | 1/1980 | Willcox |
| 4,243,619 A | 1/1981 | Fraser et al. |
| 4,469,853 A | 9/1984 | Mori |
| 4,540,753 A | 9/1985 | Cozewith et al. |
| 4,543,399 A | 9/1985 | Jenkins, III et al. |
| 4,588,790 A | 5/1986 | Jenkins, III et al. |
| 4,620,049 A | 10/1986 | Schmidt et al. |
| 4,621,952 A | 11/1986 | Aronson |
| 4,888,704 A | 12/1989 | Topliss et al. |
| 5,096,634 A | 3/1992 | Tsadares et al. |
| 5,121,337 A | 6/1992 | Brown |

(Continued)

FOREIGN PATENT DOCUMENTS

EP    238 796 A2    9/1987

(Continued)

OTHER PUBLICATIONS

Erlich, P., et al., "Fundamentals of the Free-Radical Polymerization of Ethylene," Advances in Polymer Science, vol. 7, pp. 386-448, 1970.

(Continued)

*Primary Examiner*—Gregory J Toatley, Jr.
*Assistant Examiner*—Abdullahi Nur

(57) ABSTRACT

Method and systems for online analysis of a polymeric material within a mixing device are provided. In certain embodiments, the methods and systems subject the polymeric material to Raman spectroscopy analysis. The Raman spectroscopy provides analysis of polymer properties that may include melt index, density, viscosity, molecular weight, molecular weight distribution, weight ratios of different polymers comprising the polymeric material, additive concentrations, crosslinking agent concentrations, scissoring agent concentrations, and combinations thereof. The spectroscopy results can be used to provide process control to adjust operating parameters of the mixing device and/or an associated polymerization process. The mixing device may be an extruder. The methods and systems may also include a processor for evaluating the results of the Raman analysis and automatically adjusting the mixing device and/or polymerization processes.

38 Claims, 10 Drawing Sheets

U.S. PATENT DOCUMENTS

| | | | |
|---|---|---|---|
| 5,151,474 | A | 9/1992 | Lange et al. |
| 5,202,395 | A | 4/1993 | Chambon |
| 5,270,274 | A | 12/1993 | Hashiguchi et al. |
| 5,274,056 | A | 12/1993 | McDaniel et al. |
| 5,352,749 | A | 10/1994 | DeChellis et al. |
| 5,405,922 | A | 4/1995 | DeChellis et al. |
| 5,436,304 | A | 7/1995 | Griffin et al. |
| 5,462,999 | A | 10/1995 | Griffin et al. |
| 5,589,555 | A | 12/1996 | Zboril et al. |
| 5,638,172 | A | 6/1997 | Alsmeyer et al. |
| 5,675,253 | A | 10/1997 | Smith et al. |
| 5,678,751 | A | 10/1997 | Buchanan et al. |
| 5,682,309 | A | 10/1997 | Bartusiak et al. |
| 5,696,213 | A | 12/1997 | Schiffino et al. |
| 5,864,403 | A | 1/1999 | Ajji et al. |
| 5,892,228 | A | 4/1999 | Cooper et al. |
| 5,999,255 | A | 12/1999 | Dupée et al. |
| 6,072,576 | A | 6/2000 | McDonald et al. |
| 6,144,897 | A | 11/2000 | Selliers |
| 6,204,344 | B1 | 3/2001 | Kendrick et al. |
| 6,204,664 | B1 | 3/2001 | Sardashti et al. |
| 6,218,484 | B1 | 4/2001 | Brown et al. |
| 6,228,793 | B1 | 5/2001 | Hosaka et al. |
| 6,239,235 | B1 | 5/2001 | Hottovy et al. |
| 6,281,300 | B1 | 8/2001 | Kendrick |
| 6,380,325 | B1 | 4/2002 | Kendrick |
| 6,405,579 | B1 | 6/2002 | Tjahjadi et al. |
| 6,479,597 | B1 | 11/2002 | Long et al. |
| 6,673,878 | B2 | 1/2004 | Donck |
| 7,116,414 | B2 * | 10/2006 | Long et al. ............... 356/301 |
| 2002/0156205 | A1 | 10/2002 | Long et al. |
| 2004/0198927 | A1 | 10/2004 | Battiste |
| 2004/0233425 | A1 | 11/2004 | Long et al. |
| 2004/0266959 | A1 | 12/2004 | Heslop et al. |
| 2005/0154155 | A1 * | 7/2005 | Battiste ..................... 526/72 |

FOREIGN PATENT DOCUMENTS

| | | |
|---|---|---|
| EP | 257 316 A1 | 3/1988 |
| EP | 257 316 B1 | 3/1988 |
| EP | 328 826 | 8/1989 |
| EP | 561 078 | 9/1993 |
| EP | 406 805 B1 | 12/1995 |
| EP | 561 78 B1 | 4/1997 |
| JP | 02038841 | 2/1990 |
| WO | WO 94/21962 | 9/1994 |
| WO | WO 96/41822 | 12/1996 |
| WO | WO 98/08066 | 2/1998 |
| WO | WO 99/01750 | 1/1999 |
| WO | WO 01/09201 | 2/2001 |
| WO | WO 01/09203 | 2/2001 |
| WO | WO 2004/063234 | 7/2004 |
| WO | WO 2005/049663 | 6/2005 |

OTHER PUBLICATIONS

J.M. Tedesco et al., "Calibration of dispersive Raman process analyzers," Part of the SPIE Conference on Online Chemical Process Monitoring w/Advanced Techniques, SPIE, vol. 3537, pp. 200-212, Nov. 1998.

A.C. Ouano et al., "Gel Permeation Chromatography," Polymer Molecular Weights Part II, Chapter 6, pp. 287-378, 1975.

Verstrate et al., "Near Monodisperse Ethylene-Propylene Copolymers by Direct Ziegler-Natta Polymerization. Preparation, Characterization, Properties," Macromolecules, vol. 21, pp. 3360-3371, 1988.

F. Rodriguez, "Principles of Polymer Systems 3rd Ed.," Hemisphere Pub. Corp., NY, pp. 155-160, 1989.

K.R. Beebe et al., "*An Introduction to Multivariate Calibration and Analysis,*" Analytical Chemistry, vol. 59, No. 17, pp. 1007A-1017A, Sep. 1, 1987.

J. M. Tedesco et al., "*Calibration of dispersive Raman Process Analyzers,* " The Society Of Photo-Optical Instrumentation Engineers, vol. 3537, pp. 200-212, 1999.

G.A. Bakken et al., "*Examination of Criteria for Local Model Principal Component Regression,*" Society for Applied Spectroscopy, vol. 51, No. 12, pp. 1814-1822, 1997.

M.L. Myrick et al., "*In Situ Fiber-Optic Raman Spectroscopy of Organic Chemistry in a Supercritical Water Reactor,*" Journal of Raman Spectroscopy, vol. 25, pp. 59-65, 1994.

T. Naes et al., "*Locally Weighted Regression and Scatter Correction for Near-Infrared Reflectance Data,*" Analytical Chemistry, vol. 62, pp. 664-673, 1990.

G.G. Ardell et al., "*Model Prediction for Reactor Control,*" Chemical Engineering Progress, American Institute of Chemical Engineers, vol. 79, No. 6, pp. 77-83, Jun. 1, 1983.

J.J. Zacca et al., "*Modelling of the Liquid Phase Polymerization of Olefins in Loop reactors,*" Chemical Engineering Science, vol. 48, No. 22, pp. 3743-3765, 1993.

L.P. Russo et al., "*Moving-Horizon State Estimation Applied to an Industrial Polymereization Process,*" American Control Conf. Proc., San Diego, CA, 1999.

H. Martens et al., "*Multivariate Calibration,*" Wiley & Sons Ltd., pp. viii-ix, 1989.

*Multivariate Data Analysis for Windows—Version 3.0*, excerpted from Pirouette Software Manual, Exploratory Analysis: Principal Component Analysis, pp. 5-13 through 5-40, 1985-2000.

E.P.C. Lai et al., "*Noninvasive Spectroscopic Detection of Bulk Polymerization by Stimulated Raman Scattering,*" Applied Spectroscopy, vol. 48, No. 8, 1994.

S. Sekulic et al., "*Nonlinear Multivariate Calibration Methods in Analytical Chemistry,*" Analytical Chemistry, vol. 65, No. 19. pp. 835A-845A Oct. 1, 1993.

E.D. Lipp et al., "*On-Line Monitoring Of Chlorosilane Streams By Raman Spectroscopy,*" Reprinted from Applied Spectroscopy, vol. 52, No. 1, Jan. 1998.

D.R. Battiste et al., "*On-Line Raman Analysis of Ethylene and Hexene in the Phillips 1-Hexene and Polyethylene Processes,*" Gulf Coast Conference presentation (Abstract).

M.J. Pelletier et al.; "*Optical fibers enable Raman instruments to analyze industrial process problems quickly and accurately,*" Raman Spectroscopy—Keeps Industry Under Control, Reprint: Photonics Spectra, 4 pgs., Oct. 1997.

V. Centner et al., "*Optimization in Locally Weighted Regression,*" Analytical Chemistry, vol. 70, No. 19, pp. 4206-4211, Oct. 1, 1998.

"*Principal Components Analysis,*" excerpted from PLS_Toolbox, Version 2.0 Data Analysis Manual, Eigenvector Research, Inc., pp. 32-34, 1998.

L. Markwort et al., "*Raman Imaging of Heterogeneous Polymers: A Comparison of Global versus Point Illumination,*" Applied Spectroscopy, vol. 49, No. 10, pp. 1411-1430, 1995.

I. Modric et al., "*Raman- und Infrarotspektren isotaktischer Polyalkylathylene*,*" Colloid & Polymer Sci., vol. 254, pp. 342-347, 1976.

M.G. Hansen et al., "*Real-Time Monitoring of Industrial Polymers,*" Raman Review; pp. 1-4, Mar. 1998.

S.E. Nave "*Rugged Fiber Optic Probes and Sampling Systems for Remote Chemical Analysis Via the Raman Technique,*" ISA, Paper #96-042, pp. 453-467, 1996.

M.J. Pelletier et al., "*Shining a Light on Wet Process Control,*" Semiconductor International, 4 pages, Mar. 1996.

K.P.J. Williams et al., "*Use of Micro Raman Spectroscopy for the Quantitative Determination of Polyethylene Density Using Partial Least-Squares Calibration,*" Journal of Raman Spectroscopy, vol. 26, pp. 427-433, 1995.

* cited by examiner

US 7,483,129 B2

ON-LINE PROPERTIES ANALYSIS OF A MOLTEN POLYMER BY RAMAN SPECTROSCOPY FOR CONTROL OF A MIXING DEVICE

FIELD OF THE INVENTION

This disclosure relates to methods and systems for measuring polymeric properties and controlling polymer production, finishing, and processing processes using the measured properties.

BACKGROUND OF THE INVENTION

Mixing devices such as mixers, extruders, gear pumps, and devolatizers have a long history of use in processing various types of polymeric materials. Typically the polymeric material is melted within the mixing device or prior to entry into the mixing device to facilitate processing of the polymeric material in the mixing device. Polymeric materials may be melted by simply heating the material to its melting point. Additives, including reactants and degradents, may also be introduced into the heated polymeric material.

During operation, the mixing device typically exerts pressure and stresses onto the polymeric material as necessary for product formulation. Passing the polymer through dies or into molds enables the molten polymer to be formed into a desired final shape and size of the polymer product. It is important to monitor rheological properties of the molten polymer such as melt index, density, viscosity, elasticity, polymer composition, and polymer additive composition because final product performance is dependent on these properties and because properly forming the desired shape and size of a polymer product is dependent upon how well the molten polymer flows through a die or into a mold. On-line monitoring of these properties can enable the operator to adjust operational parameters thereby ensuring that these properties are within specification.

One method currently used to measure some of these physical properties involves directing a portion of the polymer, in molten or solid form, to a process rheometer. However rheometer maintenance requirements are high, which not only increases operating costs, but due to maintenance down time exacerbates its unreliable test data results. Typically, rheometers measure the properties of the molten polymer by analyzing a slip stream are taken from a mixing device, particularly extruder mixing devices.

EP 0 238 796 A2; EP 0 406 805 A2; JP 02 038 841; and U.S. Pat. No. 6,405,579 disclose the use of rheometers to determine rheological properties of polymeric materials.

SUMMARY OF THE INVENTION

This disclosure is directed to methods and systems for determining properties of polymeric material compositions within and proximate to a mixing device. Operation and function of the mixing device may also be controlled based upon the measured properties. Operation of a polymerization process producing the polymeric material processed in the mixing device may also be controlled based upon the measured properties. The measured properties may also be used for general quality control functions and product quality analysis functions as well.

In one embodiment, the methods and systems disclosed herein provide for measurement of polymer properties such as melt index, density, viscosity, molecular weight, molecular weight distribution, modifier concentration, ratio of polymeric components, and other physical and compositional properties using Raman spectroscopy, and methods of controlling a mixing device, polymer product blending, and a polymerization process using real-time, on-line polymer property data provided by Raman spectroscopic measurements.

DETAILED DESCRIPTION OF THE INVENTION

Figure 1:
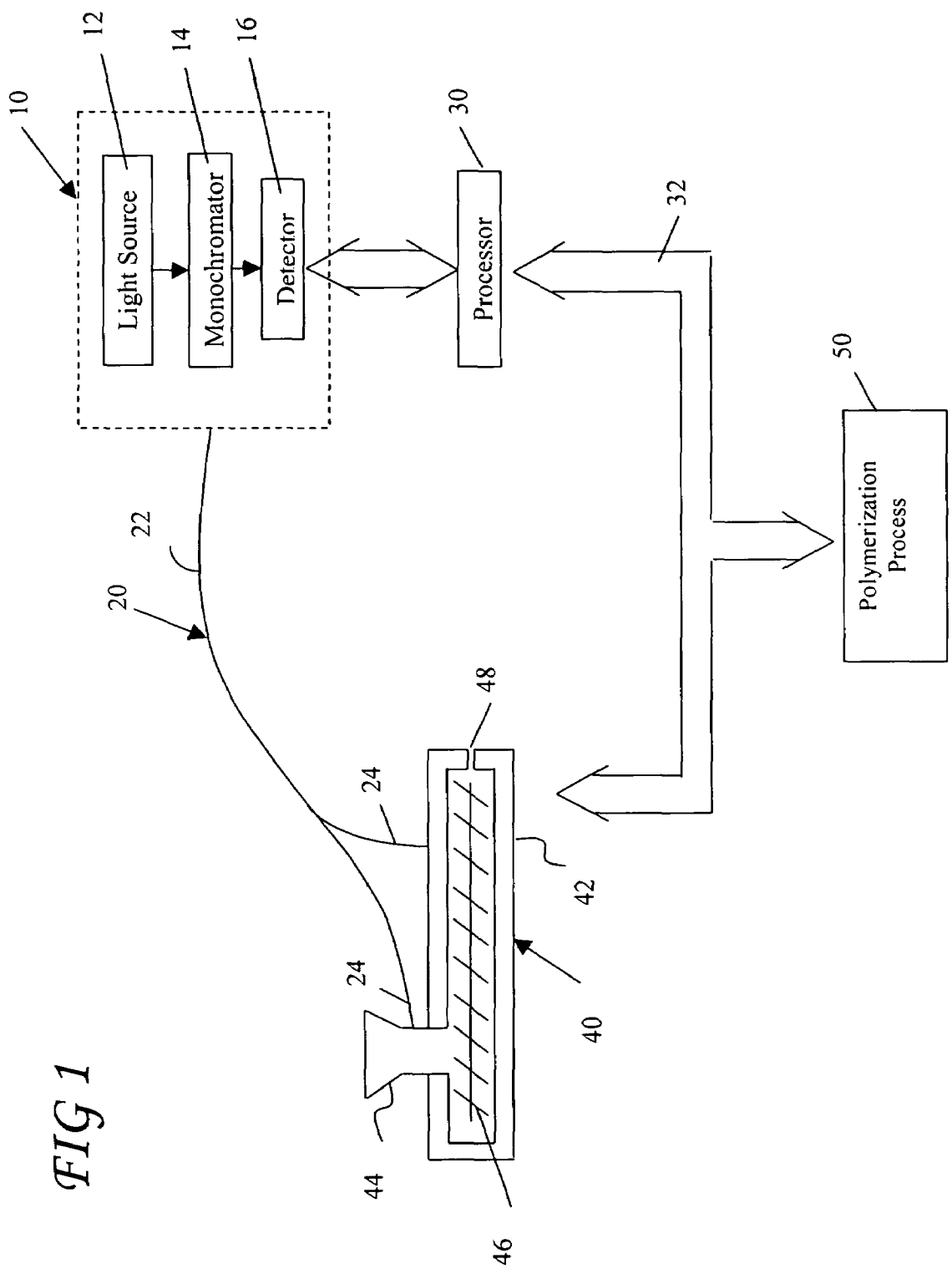
FIG. 1 is a diagram of a Raman analyzer coupled with an extrusion system.

This disclosure relates to the use of spectroscopic techniques to determine properties of a polymeric material being processed by a mixing device. The determined properties may include properties such as melt index, density, viscosity, molecular weight, molecular weight distribution, additive concentrations, weight ratios of different polymers making up the polymeric material, crosslinking agent concentrations, scissoring agent concentrations, and combinations thereof. In one embodiment, Raman spectroscopy is employed for use in this disclosure.

For purposes of this disclosure, the term "mixing device" shall be used to refer to devices such as extruders, devolatizers, gear pumps, mixers, and combinations thereof. In certain embodiments, the mixing device is selected from the group of extruders, mixers, gear pumps, and combinations thereof. In other embodiments, the mixing device may be selected from extruders, gear pumps, and combinations thereof. In still other embodiments, the mixing device is an extruder.

Raman spectroscopy is a known analytical tool for molecular characterization, identification, and quantification. Raman spectroscopy makes use of inelastically scattered radiation from a non-resonant, non-ionizing radiation source, typically a visible or near-infrared radiation source such as a laser, to obtain information about molecular vibrational-rotational states. In general, non-ionizing, non-resonant radiation is scattered elastically and isotropically (Raleigh scattering) from a scattering center, such as a molecule. Subject to well-known symmetry and selection rules, a very small fraction of the incident radiation can be inelastically and isotropically scattered, with each inelastically scattered photon having an energy $E=h\nu_0 \pm |E_{i',j'}-E_{i,j}|$, where $h\nu_0$ is the energy of the incident photon and $|E_{i',j'}-E_{i,j}|$ is the absolute difference in energy between the final (i',j') and initial (i,j) vibrational-rotational states of the molecule. This inelastically scattered radiation is the Raman scattering, and includes both Stokes scattering, where the scattered photon has lower energy than the incident photon ($E=h\nu_0-|E_{i',j'}-E_{i,j}|$), and anti-Stokes scattering, where the scattered photon has higher energy than the incident photon ($E=h\nu_0+|E_{i',j'}-E_{i,j}|$).

Raman spectra are typically shown as plots of intensity (arbitrary units) versus "Raman shift," where the Raman shift is the difference in energy or wavelength between the excitation radiation and the scattered radiation. The Raman shift is typically reported in units of wavenumbers ($cm^{-1}$), i.e., the reciprocal of the wavelength shift in centimeters. The energy difference $|E_{i',j'}-E_{i,j}|$ and wavenumbers ($\omega$) are related by the expression $|E_{i',j'}-E_{i,j}|=hc\omega$, where h is Planck's constant, c is the speed of light in cm/s, and $\omega$ is the reciprocal of the wavelength shift in centimeters.

The spectral range of the Raman spectrum acquired is broad. However, in one embodiment, a useful range includes Raman shifts (Stokes and/or anti-Stokes) corresponding to a typical range of polyatomic vibrational frequencies, generally from about 100 $cm^{-1}$ to about 4000 $cm^{-1}$. It should be appreciated that useful spectral information is present in lower and higher frequency regions. For example, numerous low frequency molecular modes contribute to Raman scattering in the region below 100 $cm^{-1}$ Raman shift, and overtone vibrations (harmonics) contribute to Raman scattering in the region above 4000 $cm^{-1}$ Raman shift. Thus, if desired, acquisition and use of a Raman spectrum as described herein can include these lower and higher frequency spectral regions.

Conversely, the spectral region acquired can be less than all of the 100 $cm^{-1}$ to 4000 $cm^{-1}$ region. For many polymers the majority of Raman scattering intensity will be present in a region from about 500 $cm^{-1}$ to about 3500 $cm^{-1}$ or from 1000 $cm^{-1}$ to 3000 $cm^{-1}$. The region acquired can also include a plurality of sub-regions that need not be contiguous. In certain embodiments, range of polyatomic vibrational frequencies acquired is about 0 $cm^{-1}$ to about 1900 $cm^{-1}$. In certain embodiments, range of polyatomic vibrational frequencies acquired is about 400 $cm^{-1}$ to about 1800 $cm^{-1}$.

As explained below, it is a particular advantage of the methods and systems described herein that Raman scattering intensity data is useful in determining properties of polymer particles without the need to identify, select, or resolve particular spectral features. Thus, it is not necessary to identify a particular spectral feature as being due to a particular mode of a particular moiety of the polymer, nor is it necessary to selectively monitor Raman scattering corresponding to a selected spectral feature. Indeed, it has been surprisingly found that such selective monitoring disadvantageously disregards a wealth of information content embedded in the spectrum that, heretofore, has generally been considered to be merely unusable scattering intensity disposed between and underlying the identifiable (and thus presumed useful) bands. Accordingly, in the methods described herein, the Raman spectral data acquired and used includes a plurality of frequency or wavelength shift, scattering intensity (x,y) measurements over relatively broad spectral regions, including regions conventionally identified as spectral bands and regions conventionally identified as interband, or unresolved regions.

The frequency spacing of acquired data can be readily determined by one skilled in the art, based on considerations of machine resolution and capacity, acquisition time, data analysis time, and information density. Similarly, the amount of signal averaging used is readily determined by one skilled in the art based on machine and process efficiencies and limitations.

In certain embodiments, the data is acquired in a continuous manner by repeating the data acquisition and analysis at designated time intervals. In specific embodiments, the data acquisition and analysis is repeated at time intervals of about 10 seconds to about 5 minutes. In specific embodiments, the data acquisition and analysis is repeated at time intervals of about 1 minute to about 5 minutes.

The spectral region measured can include Stokes scattering (i.e., radiation scattered at frequencies lower than the excitation frequency), anti-Stokes scattering (i.e., radiation scattered at frequencies higher than the excitation frequency), or both. Optionally, polarization information embedded in the Raman scattering signal can also be used, and one skilled in the art readily understands how to acquire Raman polarization information. However, determining polymer properties as described herein does not require the use of polarization information.

FIG. 1 provides a schematic representation of an exemplary embodiment of the methods and systems described herein. In the embodiment depicted, the mixing device is an extruder. Specifically, in this embodiment, a Raman spectral system is implemented to determine and monitor characteristics of a polymeric material being processed by an extruder. Although, the discussion related to FIG. 1 is provided in the context of an extruder environment, the principles of anlaysis of polymeric materials discussed in connection with FIG. 1 are applicable to polymeric materials processed by any of the variety of mixing devices described herein.

The instrumentation used to collect and process Raman data includes a Raman spectrometer system 10, a sampling system 20, a control loop 32, and a processor 30. The Raman spectrometer system 10 comprises a Raman spectrometer, the principal components of which are light source 12, a monochromator 14, and a detector 16. Raman spectrometers are well-known analytical instruments, and thus only a brief description is provided herein.

The Raman spectrometer system 10 includes a light source 12 that delivers excitation radiation to at least one probe. Scattered radiation is collected, filtered of Raleigh scattered light, and dispersed via a monochromator 14. The dispersed Raman scattered light is then imaged onto a detector 16 and subsequently processed within the processor 30, as further described below.

The excitation source and frequency can be readily determined based on considerations well-known in the art. Typically, the light source 12 is a visible or near infrared laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used. It is well-known that scattering, including Raman scattering, is proportional to the fourth power of the excitation frequency, subject to the practical limitation that fluorescence typically overwhelms the relatively weak Raman signal at higher frequencies. Thus, higher frequency (shorter wavelength) sources are preferred to maximize signal, while lower frequency (longer wavelength) sources are preferred to minimize fluorescence. One skilled in the art can readily determine the appropriate excitation source based on these and other considerations, such as mode stability, maintenance time and costs, capital costs, and other factors well understood in the art.

The excitation radiation can be delivered through a sampling system 20 terminating at a probe within the extruder, and the scattered radiation collected by any convenient means known in the art, such as conventional beam manipulation optics or fiber optic cables. For an on-line process measurement, it is particularly convenient to deliver the excitation radiation and collect the scattered radiation fiber optically. It is a particular advantage of Raman spectroscopy that the excitation radiation typically used is readily manipulated fiber optically, and thus the excitation source can be positioned remotely from the sampling region. A particular fiber optic probe is described below; however, one skilled in the art will appreciate that the Raman system is not limited to any particular means of radiation manipulation.

The scattered radiation is collected and dispersed by any convenient means known in the art, such as a fiber optic probe as described below. The collected scattered radiation is filtered to remove Raleigh scattering and optionally filtered to remove fluorescence, then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator 14 can be any such dispersive element, along with associated filters and beam manipulation optics.

The dispersed Raman scattering is imaged onto a detector 16. The choice of detector is easily made by one skilled in the art, taking into account various factors such as resolution, sensitivity to the appropriate frequency range, response time, etc. Typical detectors include array detectors generally used with fixed-dispersive monochromators, such as diode arrays or charge coupled devices (CCDs), or single element detectors generally used with scanning-dispersive monochromators, such as lead sulfide detectors and indium-gallium-arsenide detectors. In the case of array detectors, the detector is calibrated such that the frequency (wavelength) corresponding to each detector element is known. The detector response is delivered to the processor 30 that generates a set of frequency shift, intensity (x,y) data points which constitute the Raman spectrum.

The probe delivers the excitation radiation from the light source 12 to the polymeric materials, collects the scattered radiation, and the sampling system 20 delivers the scattered radiation to the monochromator 14.

With reference to FIG. 1, in operation the extruder 40 receives polymeric material for processing via the hopper 44. A variety of polymeric materials may be processed in the extruder. Exemplary polymeric materials include polyethylene, polypropylene, polyethylene terephtalate, polystyrene, polyester, synthetic rubber, and blends thereof. In certain embodiments, the polymeric materials are polyethylene, polypropylene, and blends thereof. In other embodiments, the polymeric materials are polyethylenes. Typically the polymeric composition fed to the extruder 40 is formed within an associated polymerization system 50. Often the form of the polymeric material received within the hopper 44 is in particulate, powder or granular form.

Certain characteristics of the polymeric material, such as melt index, density, viscosity, molecular weight, molecular weight distribution, additive concentrations, weight ratios of different polymers making up the polymeric material, crosslinking agent concentrations, and scissoring agent concentrations, may be determined and monitored during the extrusion process by analyzing the particular polymeric material within the hopper 44. In certain embodiments, the characteristics determined by the analyses described herein include melt index, density, viscosity, and additive concentrations, and combinations thereof. In other embodiments the characteristics determined are selected from melt index, density, and combinations thereof. As discussed above, the various characteristics may be determined by the methods and processes described herein for polymeric materials in any of the various mixing devices described herein.

The various characteristics can also be monitored by analyzing the molten material within the mixing device barrel 42 of the extruder 40. These options are illustrated in FIG. 1 where Raman probes are shown both within the hopper 44 and the mixing device barrel 42. It should be pointed out, however, that the methods and systems described herein may be utilized by analyzing only the material within the hopper 44, analyzing the material within the barrel mixing device 42, or both. In certain embodiments, the probes are positioned so that the polymeric material is in contact with the probe as the polymeric material flows past the probe.

During operation of one embodiment, the processor 30 can compare the results of the Raman analysis with baseline data to ensure that the polymeric material within the extruder 40 is within acceptable operating specifications. Should the processor 30 detect an excursion from these specifications, the processor 30 can be programmed to provide control commands to the extruder 40 or one or more related polymerization processes. Exemplary commands include a signal to increase or decrease energy input to the extruder, a signal to change the ratio of multiple polymeric materials delivered to the extruder, a signal to control the delivery of additives to the mixing device, a signal to control the identity and concentration of a crosslinking agent provided to the polymeric material, a signal to control the identity and concentration of a scissoring agent provided to the polymeric material, and a signal to control the temperature of the molten polymer within the extruder. For example, the results of the analysis may be used to provide feedback to control the delivery of melt index modifier such as oxygen and peroxides to the polymeric material to control the melt index of the polymeric material. In certain embodiments, the feedback may be used to control the melt index of the polymeric material within a range of about 0.5 to about 1.5. In certain embodiments, the signals produced are signals to increase or decrease energy input to the extruder, to change the ratio of multiple polymeric materials delivered to the extruder, and to control the temperature of the molten polymer within the mixing device.

The control commands can be delivered to the extruder 40 via the control loop 32. The processor 30 may be programmed such that it can recognize excursions from the specification and take necessary corrective actions. It is also within the scope of one skilled in the art to develop a suitable control loop 32 for carrying control commands from the processor 30 to the extruder 40.

As discussed above, the various command controls may be used in the methods and processes described herein for processing polymeric materials in any of the various mixing devices described herein.

In another embodiment, the processor 30 can affect operation of the polymerization system 50 by directing control commands to the polymerization system 50 via the control loop 32. In one embodiment, the calculated polymer product properties are compared to target polymer product properties, and at least one reactor parameter in the polymerization system 50 is adjusted based on the deviation between the calculated and target polymer product properties. Exemplary parameters that may be included among the at least one reactor parameter are monomer concentration, comonomer concentration, catalyst concentration, cocatalyst concentration, reactor temperature, the ratio of monomer feeds, the ratio of hydrogen to monomer, and combinations thereof. For example, if the chosen polymer property is density, a reactor parameter can be adjusted to increase density, such as, for example, reducing the comonomer feed rate and/or increasing the monomer feed rate. In certain embodiments, parameters that may be included among the at least one reactor parameter are selected from the group of monomer concentration, catalyst concentration, reactor temperature, and combinations thereof. In still other embodiments, parameters that may be included among the at least one reactor parameter are selected from the group of monomer concentration, reactor temperature, and combinations thereof.

For example, in the case of olefin polymerization, hydrogen can serve as a chain transfer agent. In this way, the molecular weight of the polymer product can be controlled. Additionally, varying the hydrogen concentration in olefin polymerization reactors can also vary the polymer melt flow rate, such as the melt index $I_{2.16}$ (MI). The methods and systems described herein allow control of the reactor to produce polymer having a selected MI range. This is accomplished by knowing the relationship between hydrogen concentration and the MI of polymers produced by a specific reactor, and programming the target MI or MI range into a reactor control system processor. By monitoring the polymer MI data generated by the Raman analyzer and comparing this data to the target MI range, the flow of hydrogen into the reactor vessel may be adjusted so that the MI range of the polymer product remains within the target MI range. As discussed above, the various command controls for controlling polymerization processes may be derived from analysis of polymeric materials in any of the various mixing devices described herein.

The Raman analysis data may also be used to control reactor temperature, reactor monomer and comonomer concentrations, chain transfer agent concentrations, and catalyst modifier concentrations to provide desired polymeric material properties.

It will be understood by those skilled in the art that other reactor constituent properties and other reactor parameters can be used. In a similar way as described above, the final polymer properties may be achieved by controlled metering reactor parameters in response to data generated by the Raman analyzer.

The further the mixing device is removed from the reactor, in terms of time, the less effective analysis conducted by a probe located in the mixing device will be in providing useful feedback for control of the reactor. Generally, in high pressure polymerization processes, mixing devices, such as extruders, are in close proximity to the reactor and therefore provide an effective opportunity for analysis and feedback for reactor control. In contrast, in gas phase polymerizations, because of extensive post reactor polymeric material handling requirements, although it may be accomplished, reactor control based upon analysis of polymeric material in mixing devices, particularly extruders, is less effective.

In yet another embodiment, control of both the extruder 40 and the polymerization system 50 can take place based on the results of the Raman spectroscopy. In this embodiment, the control may take place by simultaneous control of the extruder reaction process by the methods discussed above.

As noted above, the excitation radiation can be delivered to and collected from the polymeric compound by any convenient means, such as using conventional optics or fiber optic cables.

Figure 2:
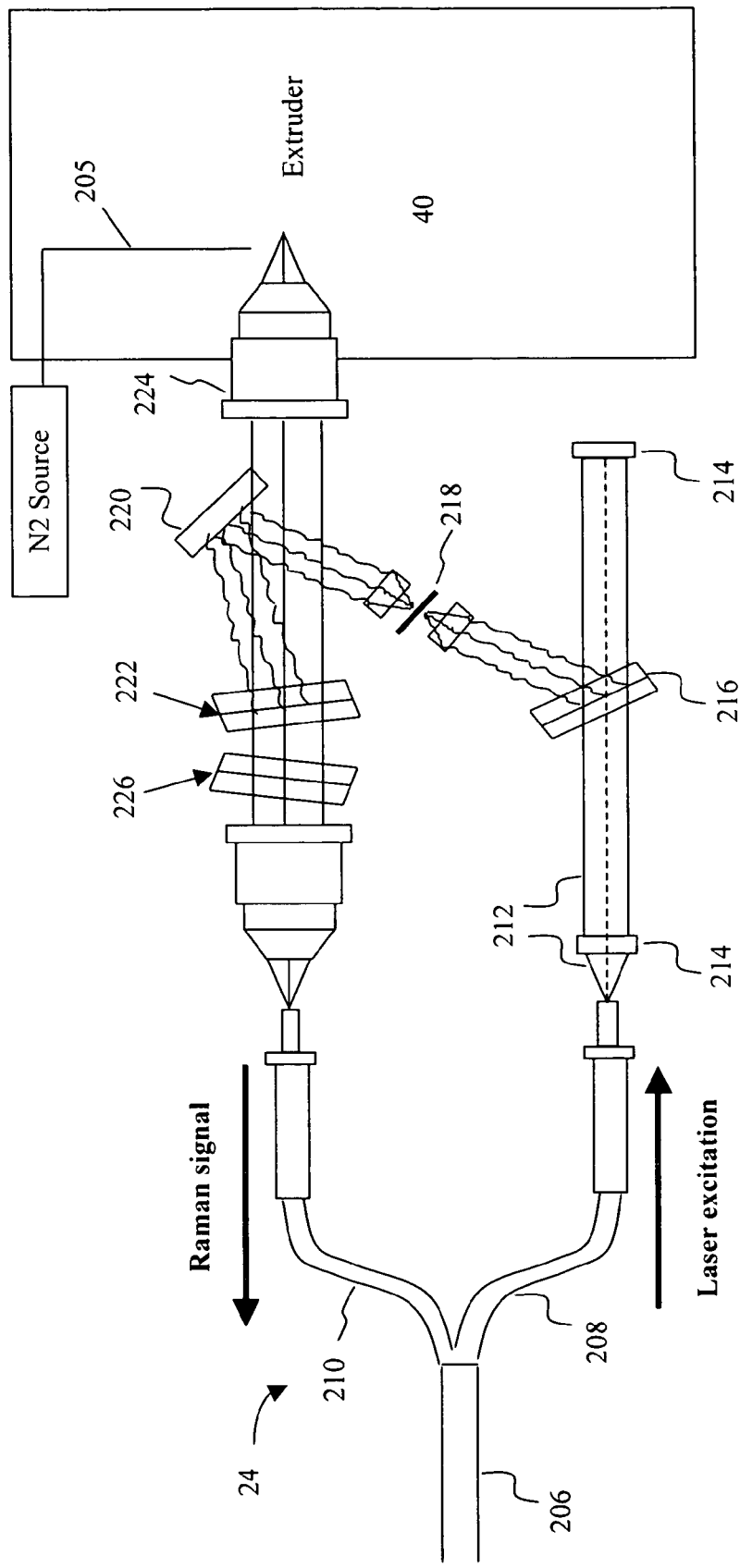
FIG. 2 depicts a fiber optic Raman probe in accordance with one embodiment of the methods and systems described herein.

FIG. 2 depicts one embodiment of a fiber optic probe that may be used in the systems and processes described herein. The probe includes a fiber optic bundle 206 including one or more fiber optic cables 208 carrying the excitation radiation from the excitation source toward the polymeric compound, and one or more fiber optic cables 210 carrying the collected scattered radiation from the polymeric compound. Fiber optic cables 208 are in optical communication with the light source 12, and fiber optic cables 210 are in optical communication with the monochromator 14. The excitation and scattered radiation can be manipulated using well-known techniques. Thus, it should be appreciated that the particular optical setup shown in FIG. 2 is merely exemplary. Excitation radiation 212 is directed via optics 214 to a holographic grating 216 and spatial filter 218 to remove silica Raman due to the fiber optic cable, then directed via mirror 220 and beam combiner 222 to sampling optics (not shown) within probe head 224. Here the probe head 224 is disposed within extruder 40. As noted above, the probe can be inserted at any position along or around the mixing device 40, and is not limited to being inserted within the barrel 42 or hopper 44. Scattered radiation is collected via the sampling optics and directed through beam combiner 222, a notch filter 226 to remove the Raleigh scattered radiation, and into fiber optic cables 210.

Because static charge may build up on the probe head 224, to dissipate static charge an optional grounding strap (not shown) can be used to ground the probe head 224 to the mixing device 40.

Optionally, an inert gas flow is provided via conduit 205. The inert gas, such as nitrogen gas, is directed via conduit 205 to provide a gas flow across the probe head 224 to reduce the incidence of probe fouling on the probe head 224. Generally, when a probe is provided in a mixing device as described herein, the friction of the polymeric material flowing past the probe eliminates the need for a purge gas stream to prevent probe fouling.

Referring again to FIG. 1, the processor 30 receives signals from the detector 16. The processor 30 can comprise a computer capable of storing and processing the Raman data. In one embodiment described above, the processor 30 controls the motion of the sampling probe. In another embodiment, the processor 30 compares the calculated value of one or more polymer properties to a target value, and adjusts one or more extruder 40 parameters in response to the deviation between calculated and target values. In yet another embodiment, the comparison of target to calculated values is relied on for adjusting the control of the polymerization system 50. Alternatively, both the polymerization process and the extruder process can be adjusted based on the comparison data.

Interiors of mixing devices present unique temperature and pressure environments in which to conduct spectroscopic analysis as described herein. In certain embodiments, the temperature surrounding the probe should be accurately determined to compensate for the shift in the scattered radiation associated with the measured temperature to ensure accurate analysis. For example, it is generally found that a shift of about ¹/₁₀ of a wave number per every ° C. increase in temperature may be used to provide more accurate analysis in mixing device as described herein. The correction may be made directly in the data generated by the analysis or by adding a term in the analysis equation used to generate the data.

The molten state of the polymeric material within a mixing device also presents a unique environment in which to conduct spectroscopic analysis as described herein. In certain embodiments, the focus of the probe is optimized for the phase existing at the probe to ensure accurate analysis. The methods and systems described herein are capable of providing analysis of the polymeric material under these varied conditions. The focus of the analysis probe may be optimized for the state of the polymeric material existing in the reaction system at the probe to ensure accurate analysis. In other words, the focus of the analysis system may be varied to analyze the polymeric material under these varied conditions. Generally, if the polymeric material is in a non-homogeneous state, a more accurate analysis will be obtained if the focus of the analysis probe is shorter. Correspondingly, if the polymeric material is in a homogeneous state, the focus of the analysis probe should be longer than used for non-homogeneous materials to ensure more accurate analysis.

In certain exemplary embodiments, an analysis probe having a focus point of about 50 μm to about 200 μm is used to analyze polymeric materials that are non-homogeneous. In other exemplary embodiments, an analysis probe having a focus point of about 50 μm to about 150 μm is used to analyze polymeric materials that are non-homogeneous. In additional exemplary embodiments, an analysis probe having a focus point of about 75 μm to about 100 μm is used to analyze polymeric materials that are non-homogeneous. In more particular exemplary embodiments, an analysis probe having a focus point of about 75 μm is used to analyze polymeric materials that are non-homogeneous In certain exemplary embodiments, an analysis probe having a focus point of about 400 μm to 700 μm is used to analyze homogeneous polymeric materials. In still other exemplary embodiments, an analysis probe having a focus point of about 500 μm to 650 μm is used to analyze homogeneous polymeric materials. In additional exemplary embodiments, an analysis probe having a focus point of about 575 μm to about 625 μm is used to analyze homogeneous polymeric materials. In more particular embodiments, an analysis probe having a focus point of about 600 μm is used to analyze homogeneous polymeric materials.

Figure 3:
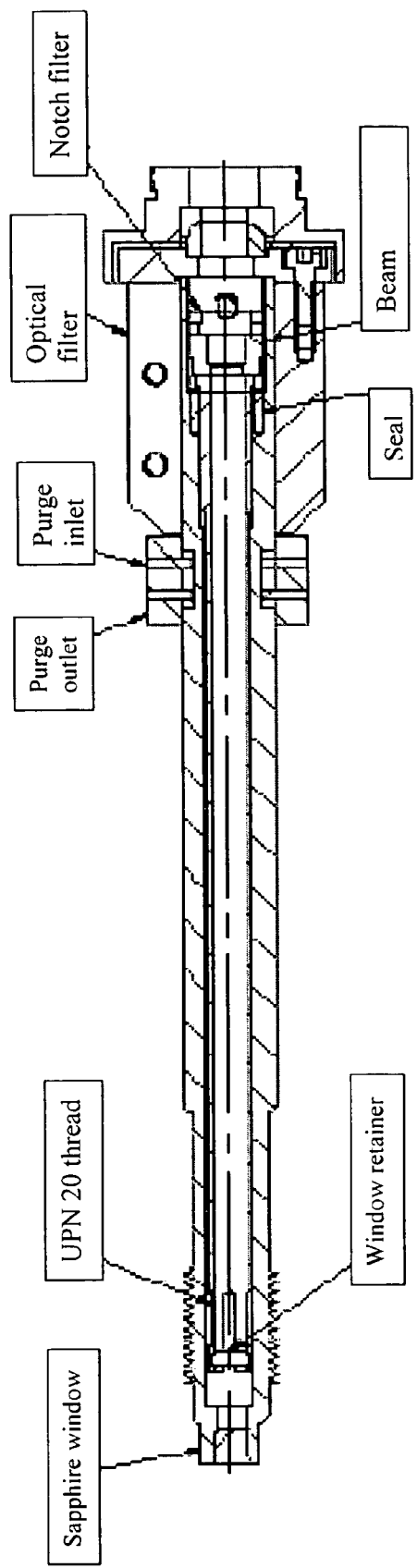
FIG. 3 depicts a Raman probe in accordance with one embodiment of the methods and systems described herein.

FIG. 3 provides a representation of another exemplary Raman probe suitable for use in accordance with the methods and systems described herein. The probe depicted in FIG. 3 is commercially available from Kaiser Optical Systems.

Experimental Evaluations

A series of experimental evaluations were conducted in which a Raman probe designed for molten polymer service was connected to a Raman spectrometer. Raman spectra were collected from a series of linear low density polyethylene material ("LDPE") samples with known values of melt index ("MI") and vinyl acetate concentration as they were fed through a laboratory extruder. A partial least squares ("PLS") regression technique was then used to develop a predictive relationship between the known values of MI and vinyl acetate concentration to the information in the Raman spectra collected.

Figure 4:
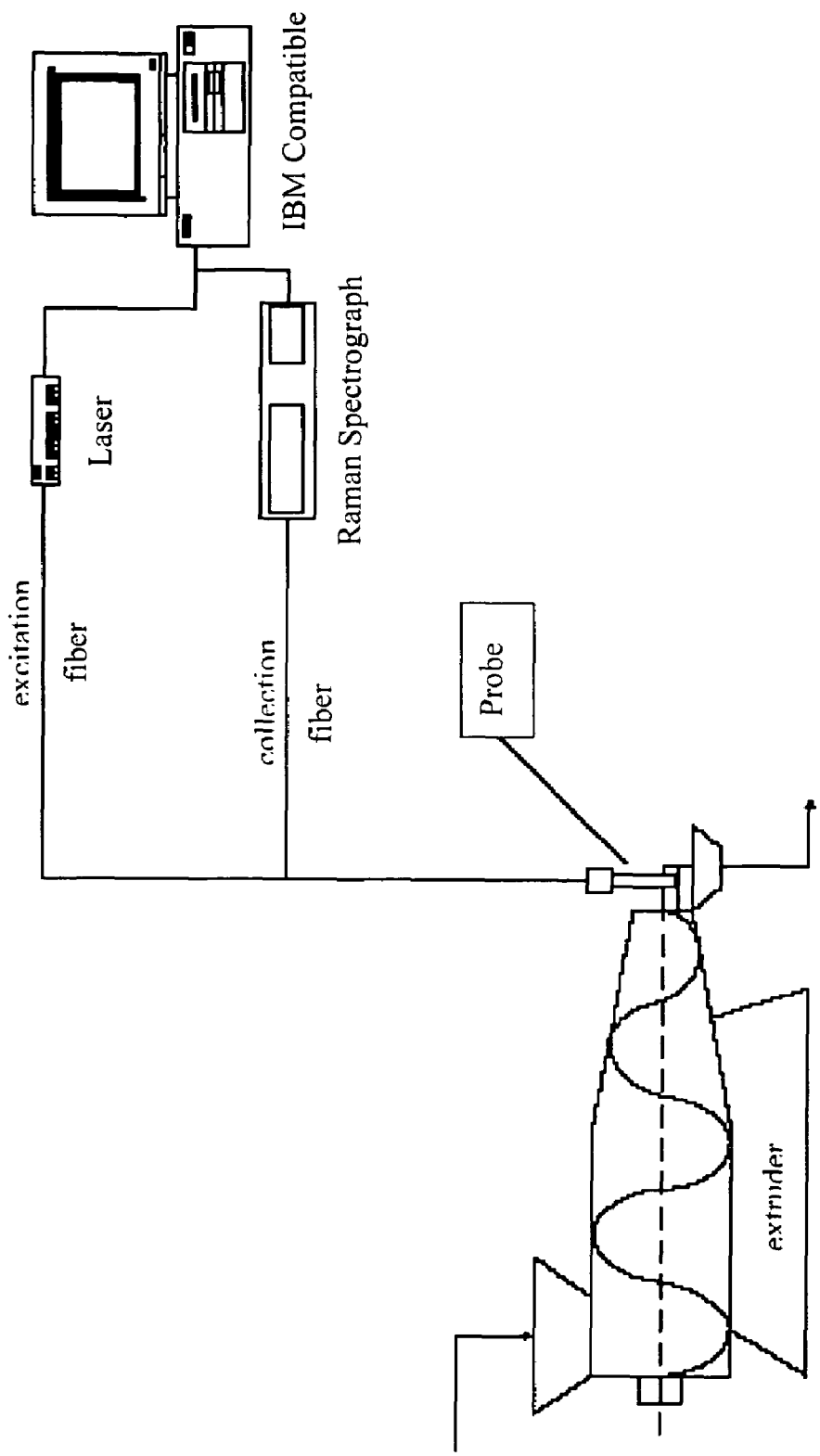
FIG. 4 depicts an equipment arrangement used to conduct experimental analysis in accordance with the methods and processes described herein.

A diagram of the experimental setup is represented schematically in FIG. 4. It includes a 12 Axiom Analytical Raman probe (12" immersion length×1" diameter) swaged into a 1" pipe-T coupled to the outlet of a 1" Killian extruder configured so that the optical window of the probe was immersed in the molten LDPE at the exit of the extruder. The probe was coupled to a 50 mW, 783 nm, multimode laser by a 100 micron, low OH, step index, silica fiber optic cable. It was coupled to a Chromex spectrograph with a 200 micron, low OH, step index, silica fiber optic cable and configured with a single diffraction grating set for nominal 6 wavenumber resolution over the frequency range between 200-2200 wavenumbers. The spectrograph was electronically coupled to a PC running Chromex's data collection software.

The extruder was continuously feed polymer, working through the entire sample set starting with the highest MI. An FT-NIR was also coupled to the extruder and used to monitor sample exchange. The rate of exchange in the extruder varied with the sample MI and took between 10 and 30 minutes. Once the FT-NIR indicated that the extruder was completely purged data was collected on the new grade for an additional 15-30 minutes. Data was archived on the system PCs hard disk for future analysis.

The data consists of a set of spectra collected on 20 LDPE samples with melt indices and vinyl acetate mole percentages as indicated in Table I.

TABLE I

| Sample | VA mole % | Melt Index |
|---|---|---|
| 1 | 28.0 | 391 |
| 2 | 19.4 | 153 |
| 3 | 18.9 | 150 |
| 4 | 27.9 | 15.1 |
| 5 | 26.9 | 141 |
| 6 | 39.0 | 60 |
| 7 | 39.1 | 57 |
| 8 | 33.0 | 43.78 |
| 9 | 32.2 | 21.01 |
| 10 | 0.00 | 19.57 |
| 11 | 9.30 | 8.26 |
| 12 | 4.80 | 7.51 |
| 13 | 4.80 | 7.34 |
| 14 | 14.7 | 5.11 |
| 15 | 4.40 | 3.08 |
| 16 | 9.50 | 3.05 |
| 17 | 6.40 | 2.34 |
| 18 | 18.1 | 1.681 |
| 19 | 19.8 | 1.83 |
| 20 | 18.2 | 1.64 |

Figure 5:
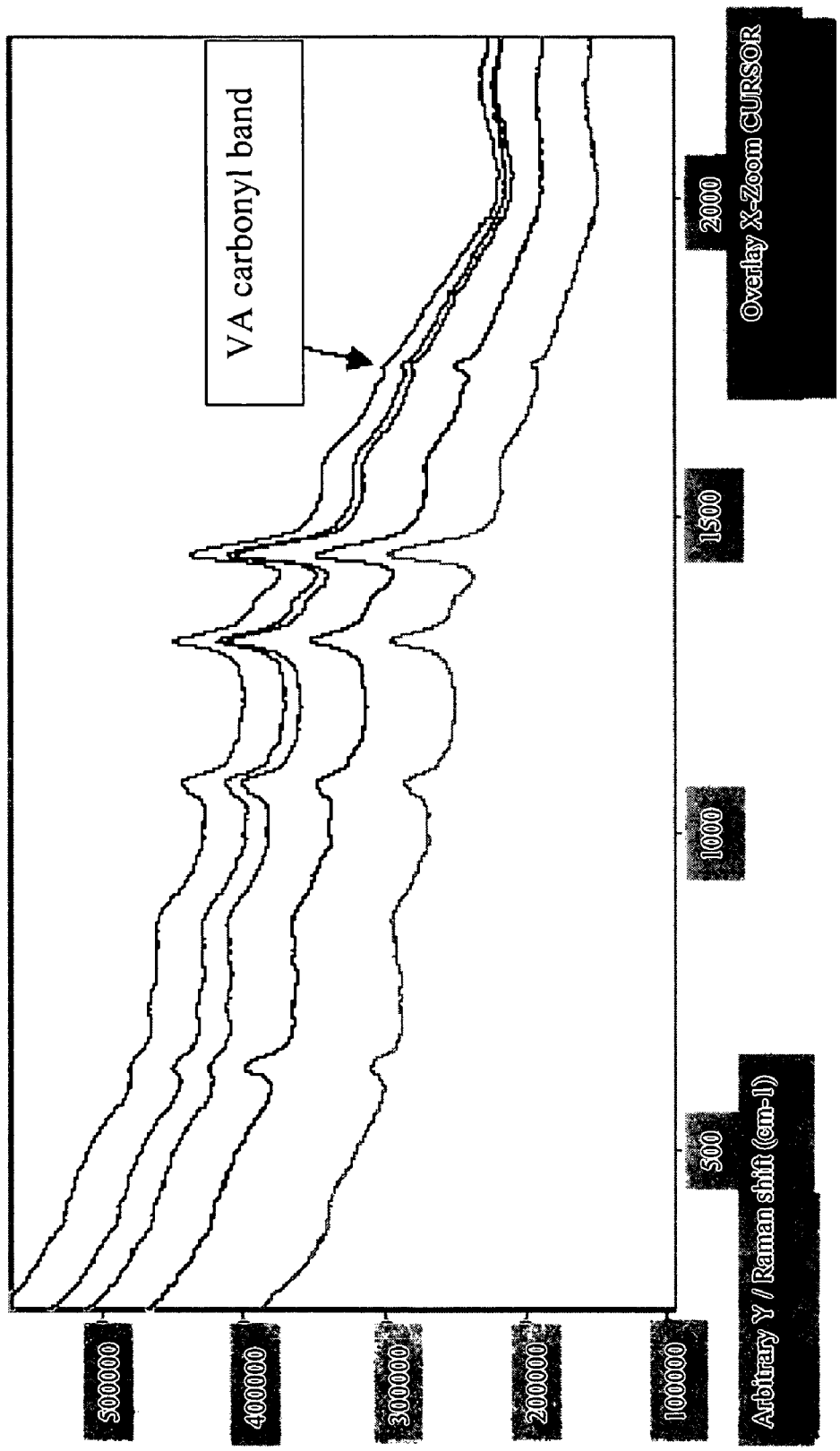
FIG. 5 provides analysis spectra representing vinyl acetate concentrations in polymeric materials.

FIG. 5 includes five spectra representing the range of vinyl acetate concentration in the data set. The y-axis scale is in unites of counts from binning the CCD columns. The x-axis unites are frequency in wavenumbers. The baselines of these spectra are in the 200,000 to 500,000 region while the baseline corrected band intensities (band intensity minus the baseline intensity) are on the order of 70,000. The reasons for this behavior are discussed below. This behavior has a direct impact on the data collection parameters.

The detector on most Raman spectrographs is a 2-dimensional CCD array of 128 or 256 rows high by 512 or 1024 columns wide. Each element accumulates charge as it is exposed to light. After a specific exposure time the total charge for each column is read into an Analog-to-Digital Converter (ADC). The ADCs are typically 16-bit meaning they have a dynamic range of 65536. Any charge larger than this over flows the ADC and is lost (i.e., the ADC becomes saturated). In order to avoid overflowing the ADC, the exposure or accumulation time for this experiment was limited to 15 seconds. Because 15 seconds was insufficient to provide adequate SNR 10 separate accumulations were added together for each spectrum.

Figure 6:
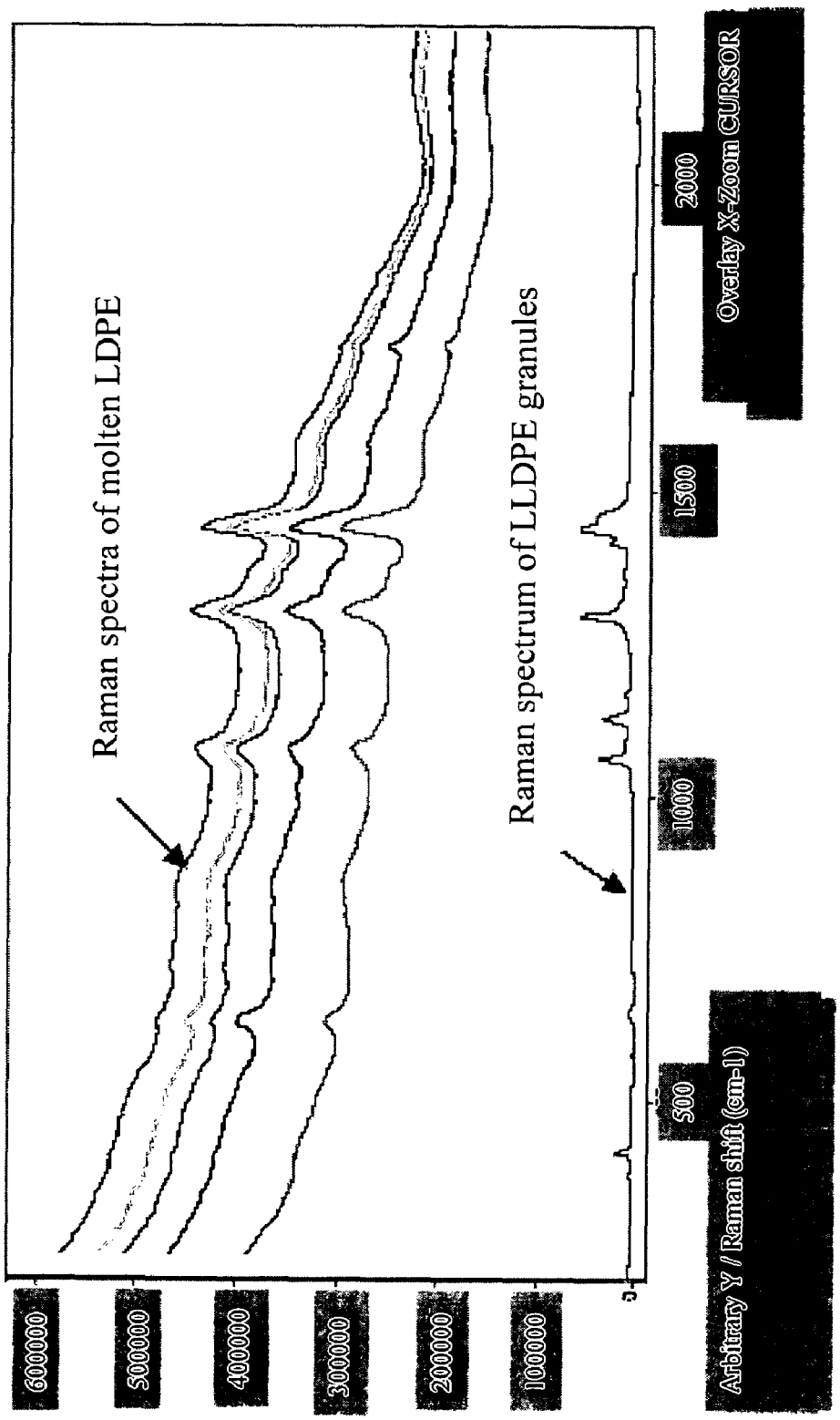
FIG. 6 provides a comparison of analysis spectra representing vinyl acetate concentrations in polymeric materials.

FIG. 6 provides a comparison of the five molten LDPE spectra from FIG. 5, a Raman spectrum measured on LLDPE granules. The collection parameters were 10- to 15-second exposures for the LDPE spectra and 1 to 15 seconds accumulation for the LLDPE spectrum. It is immediately clear that there are significant differences in the behavior of the baselines between the spectra of the two materials. It should be noted that a clear, homogenous fluid-like molten LDPE will result in better spectral data than a granular solid. What is not immediately apparent is that the SNR for the LDPE spectra is 40 and for the LLDPE spectrum it is 5,000. The reasons for these differences are discussed below. However, if it were possible to achieve SNR similar to that of the LLDPE, there should be corresponding improvements in the estimates of the measurement performance.

There are five possible reasons for the differences between the baseline and SNR behavior of the poor quality LDPE spectra and the good quality LLDPE spectrum. Fluorescence effects of additives and thermal degradation products, stray light within the spectrograph due to poorly filtered probe, thermal radiance at elevated temperatures, low power laser illumination and uncertainty to known MI and VA values and limited size of sample set.

Before discussing the analysis of the data, the effects of each of these reasons will be considered, along with the possible mechanisms for avoiding or mitigating their effects. With the exception of thermal radiance it is expected that the effects can be eliminated or reduced to an acceptable level. Thermal radiance is the primary source to the baseline behavior and there may be no practical way to reduce it other than cooling the polymer.

Materials exhibit thermal radiance where they emit broad band radiation, primarily in the infrared region of the spectrum, due to their temperature. The magnitude is a function of temperature. There are reports in the literature that at temperatures above 170° C. this effect begins to become observable in the Raman spectrum. Within limitations its effects on the measurements can be corrected for within the model, but at some point the amplitude will become large enough that the SNR of the sample spectrum will fall to a point where the measurement precision will be adversely affected.

Since LDPE temperatures are generally well below 200° C. it should not be expected to have a significant impact but since the information in the literature is very limited it would not be prudent to proceed on this assumption. The best course of action would be to design a simple experiment to quantify the effects.

Fluorescence is a phenomenon where a material absorbs energy (light) at one frequency, exciting the electronic structure into an elevated energy state and then relaxes or returns to the lower energy state (ground state) by emitting light at many difference frequencies (broad band light). The main problem encountered by Raman spectroscopy due to fluorescence is that it is much stronger than the Raman signal. While the direct interference can be corrected for if the intensity is not too large, beyond a certain point it will use up enough of the dynamic range of the detector to reduce the SNR for the sample spectrum below a useable level. While LDPE does not have a fluorescence spectrum some additives and the thermal degradation products of LDPE likely will.

Since the sample point may be upstream of where the additives are added this source of fluorescence should not be an issue except that it is potentially desirable to locate the analysis sample point downstream of where the additives are added to allow a quantitative measurement of the additives to be made.

Fluorescence due to thermal degradation products of the polymer presents a potentially significant difficulty for Raman analysis as described herein. There are two mechanisms by which we would expect to observe degradation products. The first is during a startup where the solid polymer may undergo an extended period of heating. This might result in the analyzer detecting intermittent degradation material as the extruder purges. This condition would only exist for a short period. The analysis could be ignored during this time or the analyzer control logic could be instructed to recognize and ignore data corrupted by artifacts caused by degradation products. A more significant issue arises where there is a surface opposite the Raman probe and within its field of view where degradation products could collect. This condition should be avoided in the design of the sample system.

Stray light is the condition where light is randomly scattered onto the detector without first being imaged onto the diffraction grating. With Raman spectroscopy it is usually the laser that gets into the spectrograph due to poor filtering and bounces around randomly finally striking the detector. Since even a very small amount of laser light is large when compared to the Raman signal it has the effect of producing a larger baseline offset such as observed in the LDPE spectra.

Raman intensity is directly proportional to the laser intensity and the $4^{th}$ power of the laser frequency. The laser used in these experiments was 50 mW and 785 nm. Typically a 400 mW, 785 nm laser would be used (the higher power laser was unavailable during this experiment). In the absence of interfering factors associated with fluorescence, thermal radiance and stray light, the higher power laser will result in a direct SNR enhancement of a factor of 8. This can be verified experimentally because the output of the 400 mW laser that is typically used is adjustable from 50 to 400 mW.

Prior to analysis the raw data was pretreated to remove nonspecific baseline behavior and improve SNR. Each spectrum was fit to a quadratic function which is then subtracted from the raw data to remove the offset, slope, and curvature of the baseline. The information contained in these three effects has no relationship to either the melt index or vinyl acetate concentration of the samples. In this way, the data set is orthoganalized to these effects.

Each spectrum was smoothed with a 9-point moving spline to improve SNR. The amplitude of each spectrum was normalized to the average spectrum to remove overall variations associated with variations in laser intensity, presence of varying quantities of fluorescence compounds, and other effects causing non-specific amplitude variations.

Figure 7:
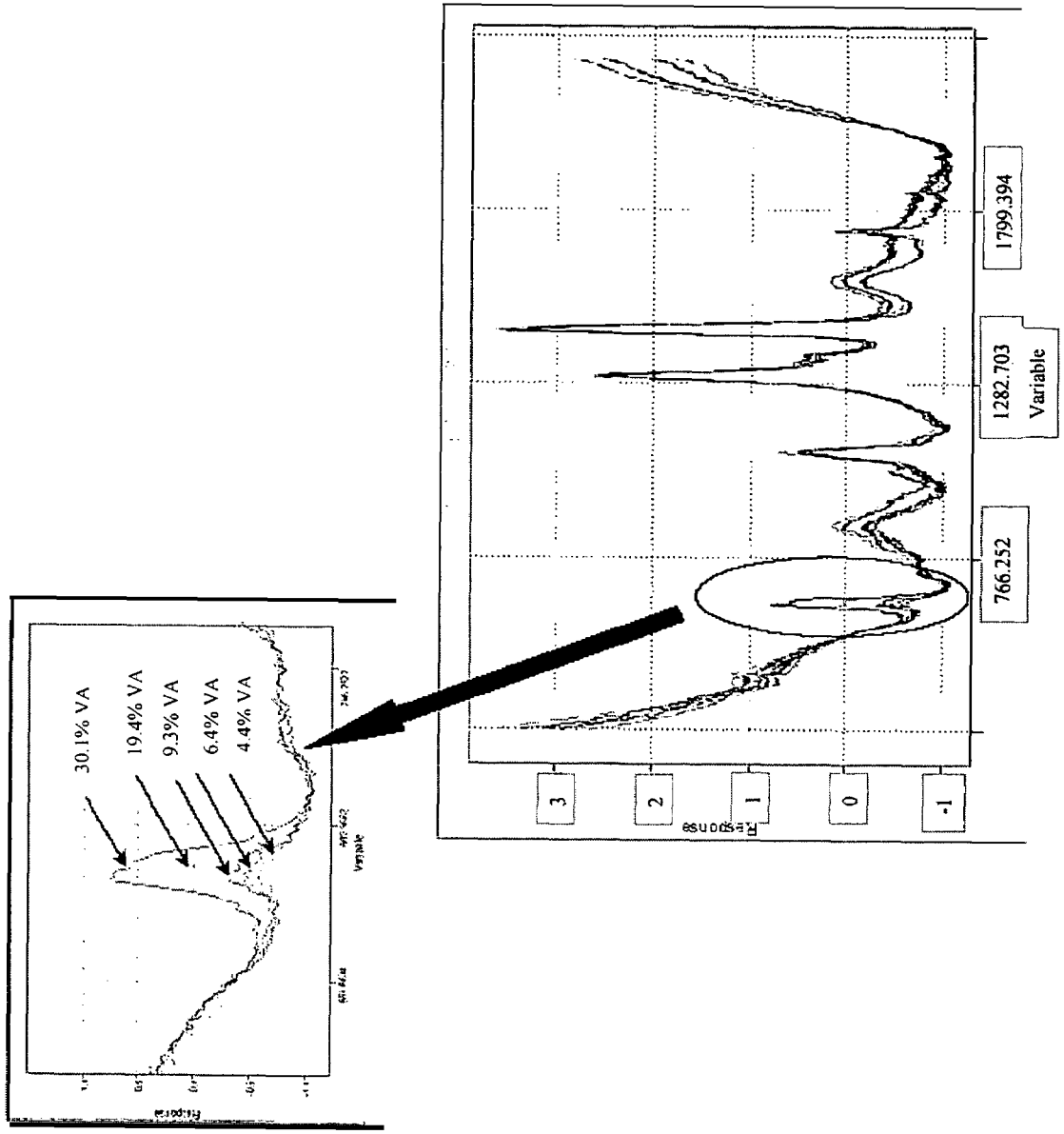
FIG. 7 provides corrected analysis spectra representing vinyl acetate concentrations in polymeric materials.

Examples of the corrected spectra are shown in FIG. 7. There are a number of specific regions in these spectra where the information is uniquely associated with the incorporated vinyl acetate concentrations and not interfered with by information associated with other components of the sample such as ethylene as exemplified in the expanded view in FIG. 7.

Figure 8:
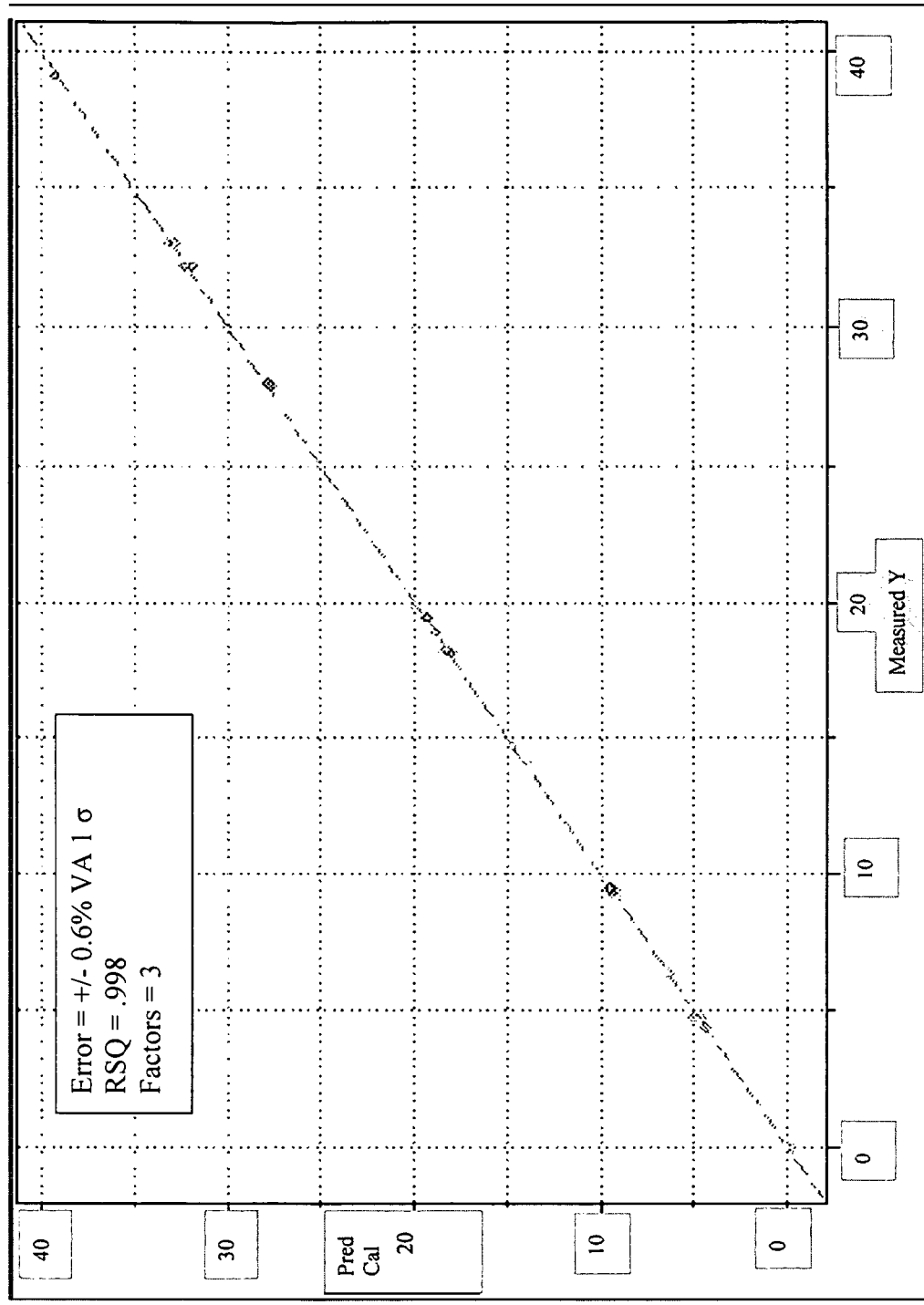
FIG. 8 represents the mathematical relationship between vinyl acetate concentrations detected in spectral data and known vinyl acetate concentrations for certain polymeric materials.

A PLS technique was used to develop a mathematical relationship between the information in the preprocessed spectral data set and the known values for vinyl acetate concentration. The results are shown in FIG. 8.

Figure 9:
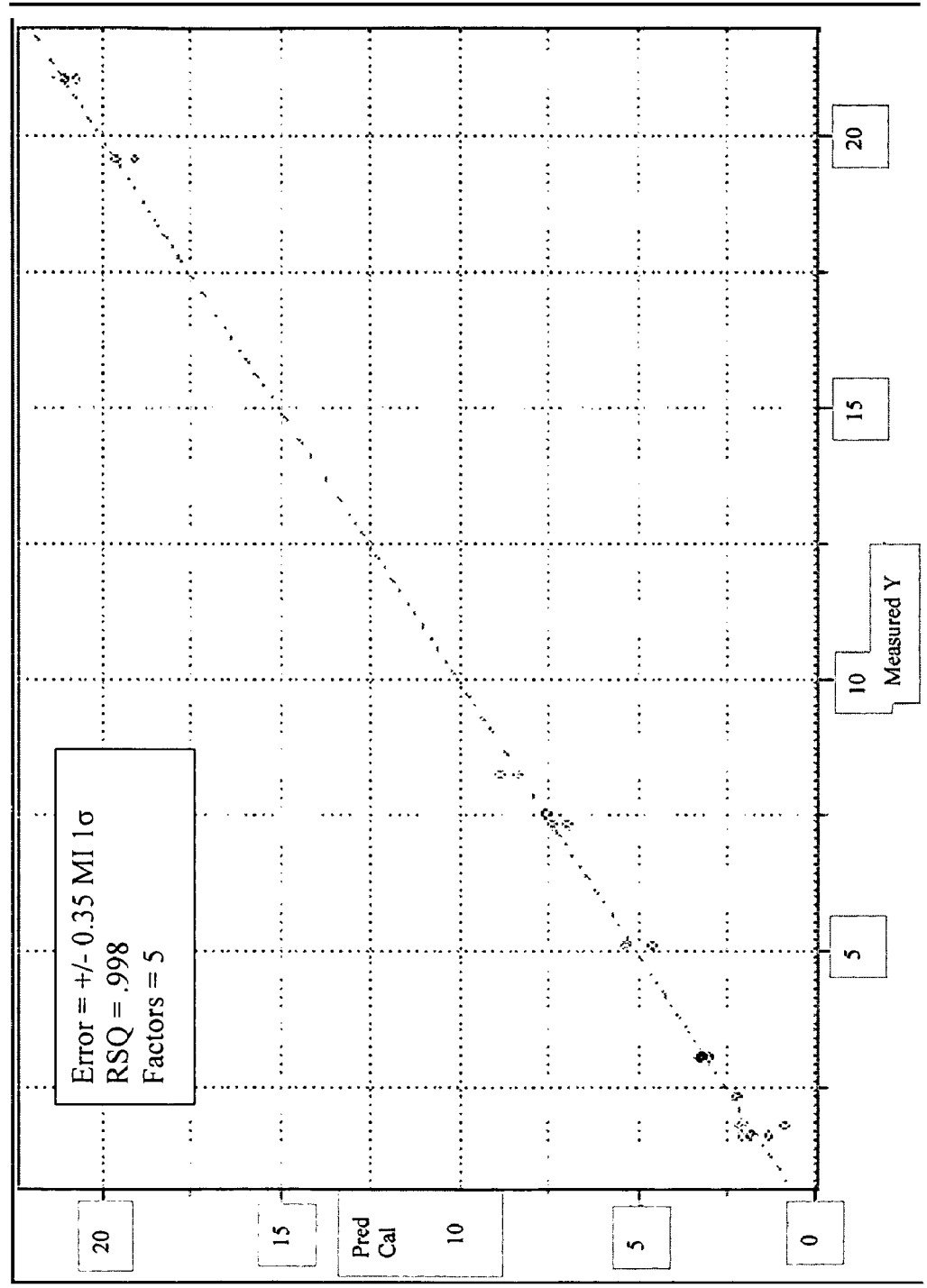
FIG. 9 represents the mathematical relationship between low range melt index values detected in spectral data and known low range melt index values for certain polymeric materials.
Figure 10:
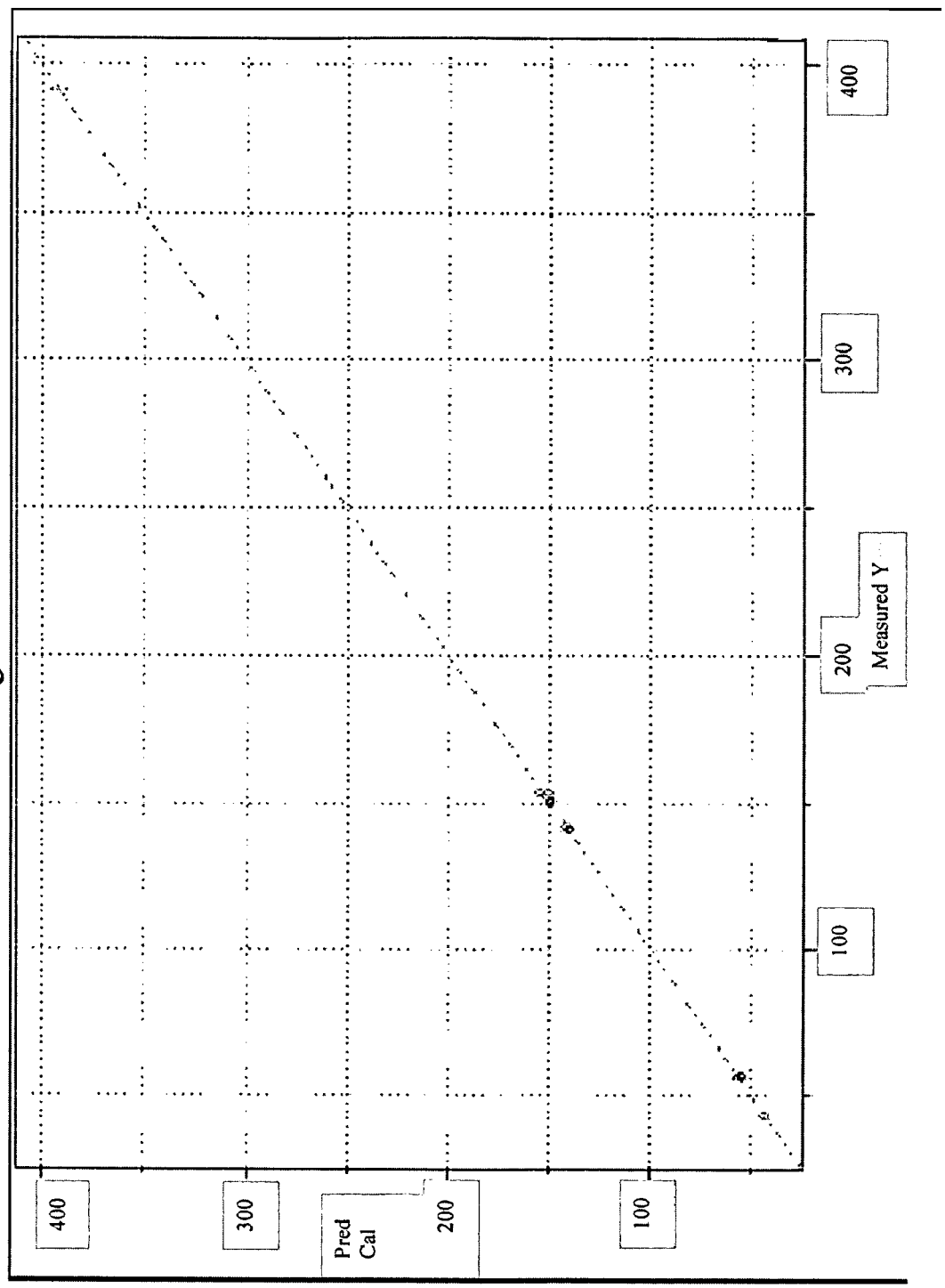
FIG. 10 represents the mathematical relationship between high range melt index values detected in spectral data and known high range melt index values for certain polymeric materials.

Estimates for the quality of a melt index measurement were developed in the same way as for the vinyl acetate concentrations. The same set of conditioned spectra along with the known values for melt index were used to develop PLS models. During the process of optimizing the model it was discovered that the best results were achieved by splitting the sample set into two melt index ranges. The low-range included samples with melt index values below 25. The remaining samples were included in the high-range. The results are shown in FIG. 9 and FIG. 10.

With respect to the various ranges set forth herein, any upper limit recited may, of course, be combined with any lower limit for selected sub-ranges.

All patents and publications, including priority documents and testing procedures, referred to herein are hereby incorporated by reference in their entireties.

Although the methods and systems described herein and their advantages have been described in detail, it should be understood that various changes, substitutions, and alterations could be made without departing from the spirit and scope of the inventions described herein as defined by the following claims.

What is claimed is:

1. A method of processing a polymeric material comprising:
   (a) directing the polymeric material to a mixing device;
   (b) irradiating at least a portion of the polymeric material;
   (c) measuring the energy shift experienced by the polymeric material due to the step of irradiating; and
   (d) determining a characteristic of the polymeric material based on the energy shift;
   wherein steps (b), (c), and (d) are conducted using at least one analysis probe and Raman spectroscopy, and wherein the polymeric material is in a homogeneous state, and the at least one analysis probe has a focus point of about 500 μm to about 650 μm.

2. The method of claim 1, wherein the characteristic of the polymeric material is selected from the group consisting of melt index, density, viscosity, molecular weight, molecular weight distribution, weight ratios of different polymers comprising the polymeric material, additive concentrations, crosslinking agent concentrations, scissoring agent concentrations, and combinations thereof.

3. The method of claim 1 further comprising repeating steps (b), (c), and (d).

4. The method of claim 3, wherein the frequency of repeating steps (b), (c), and (d) ranges from about 1 minute to about 5 minutes.

5. The method of claim 2, wherein the polymeric material is selected from the group consisting of polyethylene, polypropylene, polyethylene terephtalate, polystyrene, polyester, synthetic rubber, and blends thereof.

6. The method of claim 4, wherein the polymeric material is selected from the group consisting of polyethylene, polypropylene, polyethylene terephtalate, polystyrene, polyester, synthetic rubber, and blends thereof.

7. The method of claim 5, wherein the mixing device is selected from the group consisting of extruders, devolatizers, gear pumps, and mixers.

8. The method of claim 7, wherein the characteristic of the polymeric material is selected from the group consisting of melt index, density, viscosity, and additive concentrations, and combinations thereof.

9. The method of claim 8, wherein the mixing device is selected from the group consisting of extruders, mixers, and gear pumps.

10. The method of claim 7, wherein the mixing device is an extruder.

11. The method of claim 10, wherein the extruder comprises a barrel and a hopper.

12. The method of claim 11 further comprising irradiating the polymeric composition in at least one location selected from the group consisting of the extruder barrel, the extruder hopper, and combinations thereof.

13. The method of claim 12, wherein the step of irradiation comprises irradiating the polymeric composition with a light source having a wavelength of from about 400 $cm^{-1}$ to about 1800 $cm^{-1}$.

14. The method of claim 13, wherein the process comprises generating and transmitting a signal representative of the characteristic of the polymeric material to a processor.

15. The method of claim 14 comprising generating at least one control command with the processor and transmitting the control command from the processor to a process selected from the group consisting of an extrusion process, a polymerization process, and combinations thereof, wherein the at least one control command is based on the characteristic of the polymeric material.

16. The method of claim 15, wherein the at least one control command is provided to an extrusion process wherein the at least one control command relates to control of a parameter selected from the group consisting of energy input to the extruder, the ratio of polymeric material components delivered to the extruder, delivery of additives to the extruder, the identity and concentration of a crosslinking agent provided to the extruder, the identity and concentration of a scissoring agent provided to the extruder, the temperature of the polymeric material within the extruder, and combinations thereof.

17. The method of claim 16, wherein the at least one control command provided to the extrusion process relates to control of a parameter selected from the group consisting of energy input to the extruder, the ratio of polymeric material components delivered to the extruder, the temperature of the polymeric material within the extruder, and combinations thereof.

18. The method of claim 15, wherein the at least one control command is provided to a polymerization process wherein the at least one control command relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

19. The method of claim 18, wherein the at least one control command provided to the polymerization process relates to control of a parameter selected from the group consisting of monomer concentration, catalyst concentration, reactor temperature, and combinations thereof.

20. A process for controlling a mixing device comprising:
   (a) feeding a polymeric material to the mixing device;
   (b) irradiating at least a portion of the polymeric material within the mixing device;
   (c) measuring the energy shift experienced by the polymeric material due to the step of irradiating;
   (d) determining a characteristic of the polymeric material based on the energy shift; and
   (e) adjusting operation of the mixing device based on the characteristic of the polymeric material;
   wherein steps (b), (c), and (d) are conducted using at least one analysis probe and Raman spectroscopy, and wherein the polymeric material is in a homogeneous state, and the at least one analysis probe has a focus point of about 500 μm to about 650 μm.

21. The process of claim 20, wherein step (e) comprises generating a signal representative of the characteristic of the polymeric material and transmitting the signal to a processor.

22. The process of claim 21 comprising generating at least one control command with the processor and transmitting the control command from the processor to the mixing device.

23. The process of claim 22, wherein the mixing device is selected from the group consisting of extruders, devolatizers, gear pumps, and mixers.

24. The process of claim 23, wherein the characteristic of the polymeric material is selected from the group consisting of melt index, density, viscosity, molecular weight, molecular weight distribution, weight ratios of different polymers comprising the polymeric material, additive concentrations, crosslinking agent concentrations, scissoring agent concentrations, and combinations thereof.

25. The process of claim 24, wherein the at least one control command relates to control of a parameter selected from the group consisting of energy input to the mixing device, the ratio of polymeric material components delivered to the mixing device, delivery of additives to the mixing device, the identity and concentration of a crossliniking agent provided to the mixing device, the identity and concentration of a scissoring agent provided to the extruder, the temperature of the polymeric material within the mixing device, and combinations thereof.

26. The process of claim 25, wherein the mixing device is an extruder.

27. A process for controlling a polymerization process comprising:
 (a) feeding a polymeric material to a mixing device;
 (b) irradiating at least a portion of the polymeric material within the mixing device;
 (c) measuring the energy shift experienced by the polymeric material due to the step of irradiating;
 (d) determining a characteristic of the polymeric material based on the energy shift; and
 (e) adjusting operation of the polymerization process based on the characteristic of the polymeric material;
 wherein steps (b), (c), and (d) are conducted using at least one analysis probe and Raman spectroscopy, and wherein the polymeric material is in a homogeneous state, and the at least one analysis probe has a focus point of about 500 μm to about 650 μm.

28. The process of claim 27, wherein step (e) comprises generating a signal representative of the characteristic of the polymeric material and transmitting the signal to a processor.

29. The process of claim 28 comprising generating at least one control command with the processor and transmitting the control command from the processor to the polymerization process.

30. The process of claim 29, wherein the mixing device is selected from the group consisting of extruders, devolatizers, gear pumps, and mixers.

31. The process of claim 30, wherein the characteristic of the polymeric material is selected from the group consisting of melt index, density, viscosity, molecular weight, molecular weight distribution, weight ratios of different polymers comprising the polymeric material, additive concentrations, crosslinking agent concentrations, scissoring agent concentrations, and combinations thereof.

32. The method of claim 31, wherein the at least one control command provided to the polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

33. The method of claim 31, wherein the at least one control command provided to the polymerization process relates to control of a parameter selected from the group consisting of monomer concentration, catalyst concentration, reactor temperature, and combinations thereof.

34. The process of claim 1, wherein said polymeric material is in a homogeneous state and said analysis probe has a focus point of about 400 μm to about 700 μm.

35. The process of claim 1, wherein said polymeric material is in a non-homogeneous state and said analysis probe has a focus point of about 50 μm to about 200 μm.

36. The process of claim 20, wherein said polymeric material is in a homogeneous state and said analysis probe has a focus point of about 400 μm to about 700 μm .

37. The process of claim 27, wherein said polymeric material is in a homogeneous state and said analysis probe has a focus point of about 400 μm to about 700 μm .

38. A process for controlling a polymerization process comprising:
 (a) feeding a polymeric material to a mixing device;
 (b) irradiating at least a portion of the polymeric material within the mixing device;
 (c) measuring the energy shift experienced by the polymeric material due to the step of irradiating;
 (d) determining a characteristic of the polymeric material based on the energy shift; and
 (e) adjusting operation of the polymerization process based on the characteristic of the polymeric material;
 wherein steps (b), (c), and (d) are conducted using at least one analysis probe and Raman spectroscopy, and wherein said polymeric material is in a non-homogeneous state and said analysis probe has a focus point of about 50 μm to about 200 μm.

* * * * *